（12) United States Patent  
Ball et al.

(10) Patent No.: US 8,476,407 B2  
(45) Date of Patent: Jul. 2, 2013

(54) METALLOPEPTIDE CATALYSTS

(75) Inventors: Zachary Thomas Ball, Houston, TX (US); Brian Vincent Popp, Houston, TX (US); Alexander Nikolaevich Zaykov, Houston, TX (US)

(73) Assignee: William Marsh Rice University, Houston, TX (US)

( * ) Notice: Subject to any disclaimer, the term of this patent is extended or adjusted under 35 U.S.C. 154(b) by 56 days.

(21) Appl. No.: 12/953,075

(22) Filed: Nov. 23, 2010

(65) Prior Publication Data

US 2011/0263816 A1    Oct. 27, 2011

Related U.S. Application Data

(60) Provisional application No. 61/263,581, filed on Nov. 23, 2009.

(51) Int. Cl.
*C07K 7/00*     (2006.01)
*C07K 14/435*   (2006.01)
*C07H 21/00*    (2006.01)

(52) U.S. Cl.
USPC ................ 530/326; 530/400; 536/23.1

(58) Field of Classification Search
USPC .................. 530/326, 400; 536/23.1
See application file for complete search history.

(56) References Cited

U.S. PATENT DOCUMENTS 5,200,504 A    4/1993    Ghadiri

OTHER PUBLICATIONS

Ananias, DC and Long, EC, "Highly Selective DNA Modification by Ambient O2-Activated Co(II)-Lys-Gly-His Metallopeptides", J. Am. Chem. Soc. ,112: 10460-10461 (2000).
Franz, KJ, et al., "Lanthanide-Binding Tags as Versatile Protein Coexpression Probes", ChemBio Chem, 4:265-271 (2003).
Gilbertson, SR, et al., "Versatile Building Block for the Synthesis of Phosphine-Containing Peptides: The Sulfide of Diphenylphosphinoserine", J. Am. Chem. Soc., 116:4481-4482 (1994).
Gilbertson, SR, et al., "Synthesis of Phosphine-Rhodium Complexes Attached to a Standard Peptide Synthesis Resin", Organometallics, 15: 4678-4680 (1996).
Gilbertson, SR, et al., "Structure of Phosphorus-Containing Peptide Ligands. X-ray and NMR Structural Study of Free Ligand and Rhodium Complex", J. Org. Chem., 62: 5557-5566 (1997).
Milovic, NM, et al., "Conjugate of Palladium(II) Complex and beta-Cyclodextrin Acts as a Biomimetic Peptidase," J. Am. Chem. Soc., 126: 696-697 (2004).
Popp, BV, and Ball, ZT, "Structure-selective modification of aromatic side chains with dirhodium metallopeptide catalysts", J Am Chem Soc, 132: 6660 (2010).
Sambasivan, R, and Ball, ZT, "Metallopeptides for asymmetric dirhodium catalysis", J Am Chem Soc, 132: 9289 (2010).
Stephenson, KA, et al., "Synthesis and Screening of a Library of Re/Tc-Based Amyloid Probes Derived from beta-Breaker Peptides", Bioconjugate Chem., 19:1087-1094 (2008).
Welch, JT, et al., "Lanthanide-binding helix-turn-helix peptides: Solution structure of a designed metallonuclease", PNAS, 100(7): 3725-3730 (2003).
Zaykov, AN, et al., "Controlling Peptide Structure with Coordination Chemistry: Robust and Reversible Peptide-Dirhodium Ligation", Chem Eur J, 15: 8961 (2009).
Zaykov, AN, et al., "Helix Induction by Dirhodium: Access to Biocompatible Metallopeptides with Defined Secondary Structure", Chemistry, 16(22): 6651-6659 (2010).

*Primary Examiner* — Chih-Min Kam
(74) *Attorney, Agent, or Firm* — Boulware & Valoir (57) ABSTRACT

This application provides a metallopeptide catalyst comprising dirhodium bound to one or more carboxylate residues of a peptide, protein or peptidomimetic. These stable metallopeptides can achieve structure-selective protein modification though molecular recognition.

9 Claims, 6 Drawing Sheets

SEQUENCE LISTING

<160> NUMBER OF SEQ ID NOS: 16

<210> SEQ ID NO 1
<211> LENGTH: 21
<212> TYPE: PRT
<213> ORGANISM: Artificial Sequence
<220> FEATURE:
<223> OTHER INFORMATION: Synthetic peptide

<400> SEQUENCE: 1

Lys Ile Ser Ala Leu Lys Gln Lys Glu Ser Ala Leu Glu Gln Lys Ile
1               5                   10                  15

Ser Ala Leu Glu Lys
            20

```
<210> SEQ ID NO 2
<211> LENGTH: 21
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (8)..(8)
<223> OTHER INFORMATION: Xaa can be any naturally occurring amino acid

<400> SEQUENCE: 2

Glu Ile Ser Ala Leu Glu Lys Xaa Ile Ser Ala Leu Glu Gln Glu Ile
1               5                   10                  15

Ser Ala Leu Glu Lys
            20

<210> SEQ ID NO 3
<211> LENGTH: 18
<212> TYPE: PRT
<213> ORGANISM: Artificial Sequence
<220> FEATURE:
<223> OTHER INFORMATION: Synthetic peptide

<400> SEQUENCE: 3

Tyr Gly Lys Ala Ala Ala Ala Glu Ala Ala Glu Ala Lys Ala Ala Ala
1               5                   10                  15

Ala Lys

<210> SEQ ID NO 4
<211> LENGTH: 18
<212> TYPE: PRT
<213> ORGANISM: Artificial Sequence
<220> FEATURE:
<223> OTHER INFORMATION: Synthetic peptide

<400> SEQUENCE: 4

Tyr Gly Lys Ala Ala Ala Ala Asp Ala Ala Asp Ala Lys Ala Ala Ala
1               5                   10                  15

Ala Lys

<210> SEQ ID NO 5
<211> LENGTH: 18
<212> TYPE: PRT
<213> ORGANISM: Artificial Sequence
<220> FEATURE:
<223> OTHER INFORMATION: Synthetic peptide

<400> SEQUENCE: 5

Tyr Gly Lys Ala Ala Ala Ala Asp Ala Ala Glu Ala Lys Ala Ala Ala
1               5                   10                  15

Ala Lys

<210> SEQ ID NO 6
<211> LENGTH: 18
<212> TYPE: PRT
<213> ORGANISM: Artificial Sequence
<220> FEATURE:
<223> OTHER INFORMATION: Synthetic peptide

<400> SEQUENCE: 6

Tyr Gly Lys Ala Ala Ala Ala Glu Ala Ala Asp Ala Lys Ala Ala Ala
1               5                   10                  15
```

Ala Lys

<210> SEQ ID NO 7
<211> LENGTH: 18
<212> TYPE: PRT
<213> ORGANISM: Artificial Sequence
<220> FEATURE:
<223> OTHER INFORMATION: Synthetic peptide

<400> SEQUENCE: 7

Tyr Gly Lys Ala Ala Ala Ala Glu Ala Gly Glu Ala Lys Ala Ala Ala
1               5                   10                  15

Ala Lys

<210> SEQ ID NO 8
<211> LENGTH: 18
<212> TYPE: PRT
<213> ORGANISM: Artificial Sequence
<220> FEATURE:
<223> OTHER INFORMATION: Synthetic peptide

<400> SEQUENCE: 8

Tyr Gly Lys Ala Ala Ala Ala Glu Ala Ala Ala Glu Lys Ala Ala Ala
1               5                   10                  15

Ala Lys

<210> SEQ ID NO 9
<211> LENGTH: 9
<212> TYPE: PRT
<213> ORGANISM: Artificial Sequence
<220> FEATURE:
<223> OTHER INFORMATION: Synthetic peptide

<400> SEQUENCE: 9

Lys Ala Glu Ala Ala Ala Glu Ala Lys
1               5

<210> SEQ ID NO 10
<211> LENGTH: 18
<212> TYPE: PRT
<213> ORGANISM: Artificial Sequence
<220> FEATURE:
<223> OTHER INFORMATION: Synthetic peptide

<400> SEQUENCE: 10

Tyr Gly Lys Ala Ala Ala Ala Asp Ala Ala Ala Asp Lys Ala Ala Ala
1               5                   10                  15

Ala Lys

<210> SEQ ID NO 11
<211> LENGTH: 18
<212> TYPE: PRT
<213> ORGANISM: Artificial Sequence
<220> FEATURE:
<223> OTHER INFORMATION: Synthetic peptide

<400> SEQUENCE: 11

Tyr Gly Lys Ala Ala Ala Ala Glu Ala Gly Ala Glu Lys Ala Ala Ala
1               5                   10                  15

Ala Lys

<210> SEQ ID NO 12

```
<211> LENGTH: 18
<212> TYPE: PRT
<213> ORGANISM: Artificial Sequence
<220> FEATURE:
<223> OTHER INFORMATION: Synthetic peptide

<400> SEQUENCE: 12

Tyr Gly Lys Ala Ala Ala Ala Glu Ala Gly Ala Asp Lys Ala Ala Ala
1               5                   10                  15

Ala Lys

<210> SEQ ID NO 13
<211> LENGTH: 18
<212> TYPE: PRT
<213> ORGANISM: Artificial Sequence
<220> FEATURE:
<223> OTHER INFORMATION: Synthetic peptide

<400> SEQUENCE: 13

Tyr Gly Lys Ala Ala Ala Ala Asp Ala Gly Ala Asp Lys Ala Ala Ala
1               5                   10                  15

Ala Lys

<210> SEQ ID NO 14
<211> LENGTH: 32
<212> TYPE: PRT
<213> ORGANISM: Artificial Sequence
<220> FEATURE:
<223> OTHER INFORMATION: Synthetic

<400> SEQUENCE: 14

Ala Ala Gln Leu Gln Gln Arg Val Lys Thr Leu Lys Ala Glu Ile Ser
1               5                   10                  15

Ser Glu Ala Ser Thr Ala Asn Ser Leu Arg Gln Gln Ile Ala Gln Leu
                20                  25                  30

<210> SEQ ID NO 15
<211> LENGTH: 32
<212> TYPE: PRT
<213> ORGANISM: Artificial Sequence
<220> FEATURE:
<223> OTHER INFORMATION: Synthetic

<400> SEQUENCE: 15

Thr Asp Thr Leu Gln Lys Glu Thr Asp Gln Leu Glu Thr Glu Lys Ser
1               5                   10                  15

Ala Leu Gln Asp Glu Ile Ala Asn Leu Leu Ala Glu Lys Glu Lys Leu
                20                  25                  30

<210> SEQ ID NO 16
<211> LENGTH: 29
<212> TYPE: PRT
<213> ORGANISM: Artificial Sequence
<220> FEATURE:
<223> OTHER INFORMATION: Synthetic

<400> SEQUENCE: 16

Ala Arg Arg Lys Asn Phe Thr Phe Gln Gln Asn Ile Asn Asn Leu Lys
1               5                   10                  15

Arg Gln Glu Ala Leu Leu Glu Gln Gln Val Arg Ala Leu
                20                  25
```

METALLOPEPTIDE CATALYSTS

PRIOR RELATED APPLICATIONS

This invention claims priority to U.S. 61/263,581 filed on Nov. 23, 2009, and incorporated by reference in its entirety herein.

FEDERALLY SPONSORED RESEARCH STATEMENT

Not applicable.

FIELD OF THE INVENTION

The invention relates to catalysts, in particular to metallopeptide catalysts.

BACKGROUND OF THE INVENTION

One of the great promises of molecular biology is the possibility of creating designer proteins that can be used to deliver drugs to very specific targets or to provide novel enzymatic reactions. The redesign of a protein to include metal sites that could confer a range of enzymatic activities is particularly intriguing. Designed metalloproteins have the potential to promote natural enzymatic reactions on unnatural substrates or even to achieve reactivity through mechanisms completely unknown in biology.

To date, metallopeptide chemistry has focused largely on retaining 3D structure in a protein once a metal is introduced. U.S. Pat. No. 5,200,504, for example, describes peptides with secondary structures stabilized with transition metals, including Cu(II), Zu(II), Ni(II) and Ru(III). Metal ions are bound to amino acid side chains, for example at the side chains of histidine and cysteine residues at i and i+4 positions in a bidentate complexes to fix the peptide back bone in an alpha-helical conformation. U.S. Pat. No. 5,200,504 does not suggest dimetal-peptide adducts, for example dirhodium-peptide complexes, nor catalysis using a metal-peptide adduct. Additionally, these metallopeptides were never tested for catalytic activity, and it was not clear that the metal was truly bound instead of just loosely coordinated to the peptide (e.g., inert to ligand exchange in an aqueous environment).

Other patents describing metallopeptides are known, including for example, US2005282739. In this patent application, the metal ion is complexed with nitrogen atom and sulfur atoms from the peptide side chains of melanocyte stimulating hormone. Thus, high levels of metal ion are typically required to maintain the metal, which can be prone to oxidation and loss. Further, the metal ions are used to modify the proteins, making them useful as modulators of receptor function, but the metal does not serve any specific catalytic function therein.

Other references discussing metallopeptides include Scott R. Gilbertson, et al., Versatile Building Block for the Synthesis of Phosphine-Containing Peptides: The Sulfide of Diphenylphosphinoserine, J. Am. Chem. Soc. 1994, 116, 4481-4482; Scott R. Gilbertson, et al., Structure of Phosphorus-Containing Peptide Ligands. X-ray and NMR Structural Study of Free Ligand and Rhodium Complex, J. Org. Chem. 1997, 62, 5557-5566; Scott R. Gilbertson, et al., Synthesis of Phosphine-Rhodium Complexes Attached to a Standard Peptide Synthesis Resin, Organometallics 1996, 15, 4678-4680; Katherine J. Franz, et al., Lanthanide-Binding Tags as Versatile Protein Coexpression Probes, ChemBio Chem 2003, 4, 265-271; and Joel T. Welch, et al., Lanthanide-binding helix-turn-helix peptides: Solution structure of a designed metallonuclease, PNAS, Apr. 1, 2003, Vol. 100, No. 7 3725-3730.

While the above references may discuss metallopeptides in general that may have some catalytic function, none have dimetal adducts, such as described herein, and none are shown to be able to modify proteins and peptides.

Metal binding to natural polypeptides in an aqueous environment has typically confined to histidine, cysteine, and methionine residues to date. Certain poly-carboxylate sequences are known to bind lanthanide metals, but these are kinetically exchangeable interactions, and only very minimal catalytic activity is known and no structure-selective protein modification is shown. Except for these, carboxylate side chains are largely unexplored as sites for selective reactivity or ligation. Additionally, it is rare to find metallopeptides with non-biological metal centers ligated by natural amino-acid side chains stable to biomolecules. Furthermore, toxicity of metallopeptides is largely unexplored.

What is needed in the art therefore, is a catalyst capable of achieving enzyme-like recognition and modification of specific targets such as peptide or protein sequences. A metallopeptide capable of this catalysis in a complex biological mixture will require the development of exchange-inert metal coordination, requiring less metal and likely presenting fewer toxicity issues.

SUMMARY OF THE INVENTION

We have created metallopeptides herein that have demonstrated catalytic activity in the modification of specific peptide or protein sequences, and that are sufficiently stable as to allow use in living cells, indicating that the metal-peptide linkage is exchange-inert, rather than dynamic and fluxional. We have exemplified the invention herein with dirhodium bound to carboxylate side chains, but expect that the invention can be applied to other metal ions, such as iridium, platinum, and copper, palladium.

Dirhodium ($Rh_2$) is suited for carboxylate ligation because carboxylates coordinate via a $k^2$-orientation that bridges the Rh—Rh bond and increases stability against ligand substitution. These adducts can catalyze bond-forming processes in aqueous solution and retain catalytic activity.

Although not required for successful implementation, this application can achieve metallopeptides with macrocyclic loops formed by dirhodium chelation to one or more carboxylate side chains, with potential benefits for improved stability and structural integrity. If desired, helical secondary structure can be stabilized or induced in previously unstructured peptides as a function of the identity and spacing of carboxylate-containing residues within the polypeptide chain, for example, helix induction upon binding carboxylate side chains with i, i+3 spacing.

The peptide "scaffold" can be any peptide, protein or peptidomimetic, or non-peptide ligand for a biopolymer target. It is the scaffold that provides the catalyst with great specificity, since proteins with known binding partners (substrates, ligands, receptors and the like) can be selected and used to direct the metal catalyst to perform the desired reaction on the binding partner. Alternatively, synthetic scaffolds can be made and selected for target selectivity using known techniques.

Further, although we have demonstrated target specificity herein using peptides, it is also possible to use other scaffold molecules that have natural —COOH residues, or to which —COOH groups have been added. Thus, one could turn, e.g., a steroid molecule or other ligand into a metallosteroid or metalloligand catalyst by adding metal adducts to the steroid scaffold. A metallosteroid could thus be used to catalyze reactions in steroid receptors and other steroid binding molecules. Similarly, it should be possible to modify nucleic acid or nucleic acid-like scaffolds in a similar way. Thus, the scope of the scaffold includes any protein, nucleic acid or ligand, provided only that it have suitable locations for adding the metal adducts, and provided that the scaffold have a target binding molecule.

We have also demonstrated that the dirhodium metallopeptide is biocompatible with living embryonic kidney cells (HEK-293), highlighting broad potential of these metallopeptide catalysts for affecting biological structure and function.

We have exemplified target specific catalysis by reacting 2-styryl-2-diazoacetate esters with a variety of amino-acid side chains in model peptide systems, and also in the natural protein c-FOS. Further, we are able to achieve site specific selection of side chains for catalysis by modifying the metallopeptide catalyst, since placement of the dimetal adduct affects which side chains will be modified in the target. However, these reactions are exemplary only and we expect that the metal catalysts can be used for any reaction where molecular recognition with a biopolymer substrate is combined with catalytic transition-metal reactions, including ester formation, reductive amination, C—H activation, oxidation, and cross coupling.

Additional applications include affinity or fluorescent labeling of natural proteins for biochemical studies that are minimally disruptive of natural structure and function. Additionally, the method may allow the discovery of new protein-protein interaction and thus of new potential drug targets through the use of covalent modification as a marker for non-covalent interactions.

In more detail, the invention is directed to a catalyst comprising a transition-metal complex attached to a peptide or peptidomimetic or other scaffold, wherein the transition-metal complex has at least two metals independently selected from the group consisting of Rh, Co, Pt, Cu, Zn, Fe, Mo, Mg, Mn, Ni, Ir, and homo- and hetero-polymetallic mixtures thereof, wherein said catalyst has catalytic activity in an aqueous environment, and wherein said peptide or peptidomimetic is capable of delivering the catalyst to a target binding partner on the basis of molecular recognition of the target binding partner by the scaffold.

The catalyst is capable of catalyzing any reaction typically catalyzed by such metals, and includes without limitation, esterification, reductive amination, C—H activation, oxidation, and cross coupling reactions.

In some embodiments, the invention is a catalyst of Formula I,

(Formula I)

wherein each X is independently O, NR or NH;
  each R is independently alkyl, wherein when an X is NR, said X and the R joined to the same carbon atom are optionally taken together to form a ring containing the carbon to which they are joined;
  each M is independently selected from the group consisting of Rh, Co, Pt, Cu, Zn, Fe, Mo, Mg, Mn, Ni, and Ir;

$X^1$ is a residue in a scaffold having a carboxylic acid side chain; and $X^2$ is a hydrogen, or a residue in said scaffold having a carboxylic acid side chain; and the scaffold serves to direct the catalyst to some cognate binding partner, thus achieving very specific catalytic reactions.

In preferred embodiments, the metallopeptide catalyst has Formula II, (Formula II)

wherein each R is independently alkyl,
  X' is a residue in a peptide or peptidomimetic scaffold having a carboxylic acid side chain; and
  $X^2$ is a hydrogen, or a residue in said scaffold having a carboxylic acid side chain; and
  wherein said metallopeptide catalyst modifies a target recognized by said scaffold.

Methods of using catalyst are also provided, wherein the scaffold serves to direct the catalyst to the binding partner for scaffold (e.g., a receptor will bind its ligand, antibodies bind antigen, proteins bind substrates, etc.). Thus, target specific catalyst can be achieved by judicious selection of scaffold. Separate binding domains can also be fused to synthetic catalysts to achieve targeted delivery.

DESCRIPTION OF EMBODIMENTS OF THE INVENTION

The following abbreviations are used herein:

| | |
|---|---|
| Ac | Acetyl (—C(O)CH$_3$) |
| CD | Circular Dichroism |
| COSY | Correlated spectroscopy |
| DMEM | Dubelcco's modified eagle medium |
| ESI-MS | Electrospray ionization mass spectrometry |
| FBS | Fetal bovine serum |
| HPLC | High pressure liquid chromatography |
| LC-MS | Liquid chromatography mass spectrometry |
| MALDI-TOF | Matrix-assisted laser desorption ionization time-of-flight |
| MS | Mass spectrometry |
| NMR | Nuclear magnetic resonance |
| NOE | Nuclear Overhauser Effect |
| OAc | Acetate (—OC(O)CH$_3$) |
| TFA | Trifluoroacetic acid |
| PYRR | Pyrrolidine |

"Amino acid" refers to a molecule consisting essentially of an amine group, a carboxylic acid group and a variable side chain. An amino acid has the general formula H$_2$NCH(R)(COOH), wherein R is the side chain. Of particular interest are aspartic acid (Asp) and glutamic acid (Glu), which have carboxylic acid (—COOH) groups on their side chains. In an alpha amino acid, the amino group is attached to the carbon atom immediately adjacent to the carboxylate group (the α-carbon). Other types of amino acids exist wherein the amino group is attached to another carbon atom, for example, in gamma-amino acids such as gamma-amino-butyric acid where the carbon atom to which the amino group attaches is separated from the carboxylate group by two other carbon atoms.

Amino acids include natural and non-natural acid acids. Natural amino acids include, but are not limited to, alanine, arginine, asparagine, aspartic acid, cysteine, glutamic acid, glutamine, glycine, histidine, isoleucine, leucine, lysine, methionine, phenylalanine, proline, serine, threonine, tryptophan, tyrosine, valine, selenocysteine, pyrrolysine, ornithine, and taurine. The subset of natural amino acids naturally encoded by codons in the genome is referred to as "canonical amino acids". Natural amino acids typically have L-stereochemistry at the alpha carbon, and an amino acid that is part of a peptide or protein is called a "residue".

Non-natural (or unnatural) amino acids refer to amino acids that do not occur in nature and, thus, must be incorporated into a peptide or protein by molecular biological or chemical biological techniques, presenting a substantial barrier to research. Examples of non-natural amino acids are numerous, representing a host of chemical variations on natural amino acids by including unnatural functional groups, for example aldehyde, ketone, azide, alkenyl, alkynyl (e.g., propargyl), or ether, or including unnatural chemical elements, such as boron. For example, unnatural variations on phenylalanine include, but are not limited to, p-acetylphenylalanine, m-acetylphenylalanine, p-(3-oxobutanoyl)-1-phenylalanine, (2-amino-3-hydroxyethyl)phenylalanine, p-isopropylthiocarbonyl-phenylalanine, p-ethylthiocarbonyl-phenylalanine, p-propargyloxyphenylalanine, p-azidophenylalanine, phenylselenidylalanine, p-benzoyl-1-phenylalanine, and p-borono-phenylalanine. Use of unnatural amino acids in molecular biology is sometimes referred to as an "expanded genetic code".

"Peptide" usually refers to short polymers of amino acids linked by amide bonds (also called "peptide bonds"). However, the term is intended herein to refer to short peptides and full length proteins.

"Peptidomimetic" refers to a protein- or peptide-like chain designed to mimic a peptide. Modifications involve changes to the peptide that do not occur naturally, such as altered backbones and the incorporation of unnatural amino acids. These modification typically arise either from modification of an existing peptide, or by designing similar systems that mimic peptides, such as peptoids, β-peptides, and D-peptides.

"Peptoid" refers to a polymer comprising poly-N-substituted glycines whose side chains are appended to the nitrogen atom of the peptide backbone rather than to the a-carbon as they are in peptides. As such, a peptoid has the general formula HN(R)CH$_2$COOH, wherein R is the side chain attached to the nitrogen.

"β-Peptide" refers to an amino acid with an additional methylene (—CH$_2$—) in the peptide backbone, as compared to α-amino acids. β-Amino acids typically have the formula NH$_2$CH$_2$CH(R)(COOH), wherein R is the side chain on the β-carbon.

"D-Peptide" refers to peptide comprising amino acids with D-stereochemistry, instead of L-stereochemistry as is typically found in natural amino acids.

"Metallopeptide" refers to a peptide or peptidomimetic comprising at least one metal atom. The metal can have other ligands, for example, acetoxy. The metal can be selected from the group consisting of rhodium, cobalt, platinum, copper, zinc, iron, molybdenum, magnesium, manganese, nickel, and iridium. In a particular embodiment, the metal is rhodium.

Position i refers to the first position of a peptide sequence. Consequentially, position i+2 is 2 amino acids away from position i, position i+3 is 3 amino acids away, and position i+4 is 4 amino acids away.

In other embodiments, the peptide comprises only natural amino acids. In yet other embodiments, the metallopeptide can have the following structure:

wherein, X can be the S, NR, NH, or O. In some embodiments, X is O. In other embodiments, X is NH. R can be substituted or unsubstituted, branched or unbranched alkyl. For example, unsubstituted alkyl can be selected from the group consisting of methyl, ethyl, propyl, and butyl. In a particular aspect of this embodiment, when X is N, said X and the R bound to the same carbon are taken together to form a ring containing the carbon. At least one of $X^1$ or $X^2$ is from a COOH containing residue from a peptide (the —COOH being adducted to the M as shown herein), and is otherwise a H or short chain alkyl.

The present invention is exemplified with respect to metallopeptide catalysts containing a dimetal adduct. However, these metallopeptides are exemplary only, and the invention can be broadly applied to any peptide, peptidomimetic, or protein. The following examples are intended to be illustrative only, and not unduly limit the scope of the appended claims.

EXAMPLE 1

Dirhodium Metallopeptides

Peptides were prepared having 18 amino acids and a propensity toward helicity due to an alanine-rich sequence (Table 1). A complete turn of an α-helix requires about three or four amino acids, so carboxylate side chains (Asp, Glu) were placed in an i, i+3 or an i, i+4 relationship. Free peptides exhibit some degree of helicity in water. Owing to the helix-disrupting properties of Asp residues, peptides containing this amino acid exhibited less helicity than sequences containing Glu.

and i, i+4 carboxylate spacing. Circular dichroism (CD) spectroscopy assessed the effect of dirhodium binding on helicity.

In the i, i+4 series, both Asp (DD4) and Glu (EE4) peptides exhibited increased helicity on binding dirhodium (not shown). The effect of binding was most pronounced for Asp, wherein the helix destabilizing influence of hydrogen bond-

TABLE 1

| Entry | Peptides | Sequence/Yield[a] | $[\theta]_{220}$[b] | $f_H$[c] | $f_H$ (TFE)[d] | Rel. Hel %[e] |
|---|---|---|---|---|---|---|
| 1 | EE3 | Ac-YGKAAAAEAAEAKAAAAK-NH$_2$ SEQ ID No: 3 | −11.5 | 39 | 44 | 70 |
| 2 | EE3-Rh$_2$(OAc)$_2$ | 70 | −13.8 | 45 | 51 | 82 |
| 3 | EE3-Rh$_2$(pyrr)$_2$-iso A | 50 | −12.6 | 42 | 47 | 76 |
| 4 | EE3-Rh$_2$(pyrr)$_2$-iso B | 29 | −10.4 | 36 | 40 | 65 |
| 5 | (EE3)$_2$Rh$_2$-iso A | 25 | −7.7 | 26 | 31 | 51 |
| 6 | (EE3)$_2$Rh$_2$-iso B | 25 | −7.6 | 25 | 31 | 50 |
| 7 | DD3 | Ac-YGKAAAADAADAKAAAAK-NH$_2$ SEQ ID No: 4 | −5.3 | 21 | 24 | 39 |
| 8 | DD3-Rh$_2$(OAc)$_2$ | 80 | −1.5 | 10 | 12 | 19 |
| 9 | DE3 | Ac-YGKAAAADAAEAKAAAAK-NH$_2$ SEQ ID No: 5 | −8.0 | 29 | 32 | 52 |
| 10 | DE3-Rh$_2$(OAc)$_2$ | 67 | −0.9 | 11 | 10 | 16 |
| 11 | ED3 | Ac-YGKAAAAEAADAKAAAAK-NH$_2$ SEQ ID No: 6 | −11.4 | 38 | 43 | 70 |
| 12 | ED3-Rh$_2$(OAc)$_2$ | 59 | −1.7 | 11 | 12 | 20 |
| 13 | EE3G | Ac-YGKAAAAEAGEAKAAAAK-NH$_2$ SEQ ID No: 7 | −2.5 | 13 | 15 | 24 |
| 14 | EE3G-Rh$_2$(OAc)$_2$ | 80 | −9.6 | 33 | 38 | 61 |
| 15 | EE4 | Ac-YGKAAAAEAAAEKAAAAK-NH$_2$ SEQ ID No: 8 | −12.3 | 41 | 46 | 75 |
| 16 | EE4-Rh$_2$(OAc)$_2$ | 65 | −17.3 | 55 | 62 | 100 |
| 17 | trans-EE4-Rh$_2$(OAc)$_2$ | 19 | 0.3 | 5 | 6 | 10 |
| 18 | (EE4)$_2$Rh$_2$-A | 30 | −9.8 | 31 | 38 | 62 |
| 19 | (EE4)$_2$Rh$_2$-B | 24 | −11.0 | 34 | 42 | 68 |
| 20 | sEE4 | Ac-KAEAAAEAK-NH$_2$ SEQ ID No: 9 | −0.4 | 9 | 8 | 13 |
| 21 | sEE4-Rh$_2$(OAc)$_2$ | 58 | −11.6 | 48 | 44 | 71 |
| 22 | DD4 | Ac-YGKAAAADAAADKAAAAK-NH$_2$ SEQ ID No: 10 | −5.7 | 22 | 25 | 41 |
| 23 | DD4-Rh$_2$(OAc)$_2$ | 73 | −16.0 | 51 | 58 | 94 |
| 24 | EE4G | Ac-YGKAAAAEAGAEKAAAAK-NH$_2$ SEQ ID No: 11 | −1.9 | 12 | 13 | 21 |
| 25 | EE4G-Rh$_2$(OAc)$_2$ | 73 | −8.3 | 30 | 34 | 54 |
| 26 | trans-EE4G-Rh$_2$(OAc)$_2$ | 65 | 0.5 | 5 | 6 | 9 |
| 27 | ED4G | Ac-YGKAAAAEAGADKAAAAK-NH$_2$ SEQ ID No: 12 | −1.1 | 9 | 10 | 17 |
| 28 | ED4G-Rh$_2$(OAc)$_2$ | 57 | −12.1 | 40 | 46 | 74 |
| 29 | DD4G | Ac-YGKAAAADAGADKAAAAK-NH$_2$ SEQ ID No: 13 | −1.1 | 9 | 11 | 17 |
| 30 | DD4G-Rh$_2$(OAc)$_2$ | 70 | −10.8 | 37 | 41 | 67 |

[a]%,
[b]Residual molar ellipticity in [deg cm$^2$ dmol-res-1 · 10$^3$].
[c]Helicity content calculated as $f_H = ([\theta]220 - [\theta]c)/([\theta]inf - [\theta]c)$, where $[\theta]c = 2220 - 53T$, $[\theta]inf = (-44000 + 250T)(1 - k/Np)$, T is temperature in degrees Celsius, k = 3.0 and Np is number of peptide units.
[d]Helicity content calculated with $[\theta]inf = [\theta]220$ of EE4 in 100% TFE.
[e]Relative helicity calculated with $[\theta]inf = [\theta]220$ of EE4-Rh$_2$(OAc)$_2$.
Because each peptide has an unstructured YG tag at the N-terminus, calculated helicity values likely underestimate helicity for the rest of the peptide.

The peptides reacted with cis-Rh$_2$(OAc)$_2$(TFA)$_2$, producing adducts with bridging dirhodium centers for both i, i+3 ing from the carboxylate side chain to the amide backbone disappears upon binding dirhodium.

For peptides with i, i+3 carboxylate spacing, the free peptide EE3 is helical in solution, and binding to a dirhodium center increased helical, content, in line with i, i+4 examples discussed above. The structural requirements for helix stabilization in i, i+3 peptides are stricter than those in the i, i+4 case: Sequences with at least one Asp residue binding to dirhodium (peptides DD3, ED3, and DE3) completely disrupt helicity upon binding to dirhodium. The extra methylene in the Glu side chain may help to properly position at the dirhodium center. Although residues at i, i+3 spacing are proximal in space in a helical structure, the side chains project in different directions.

Glycine, a powerful helix-disrupting residue, was introduced into peptide sequences at the i+2 position. Glycine-containing peptides had a random-coil structure in aqueous solution, but CD analysis of the metallopeptide adducts indicated a helical structure. For peptides with i, i+4 spacing, as before, helix induction was observed regardless of whether the binding residues are Asp or Glu. A glycine-containing peptide with i, i+3 carboxylate spacing (EE3G) was also prepared. The peptide EE3G is a random coil when unbound but becomes helical following ligation to dirhodium, as evidenced the negative feature at 220 nm (not shown).

EXAMPLE 2

Metallopeptides in a Biological Environment

Transition metals, including those in metallopeptide structures, are often toxic to living cells and can easily exchange ligands in biologically relevant environments. One complication is that biological pH is near the upper end of the stability range for dimetal adduct, particularly for dirhodium-carboxylate linkages. To examine both toxicity and stability simultaneously, living human embryonic kidney stem cells (HEK-293) were incubated in 10% FBS and DMEM buffer with EE4G-$Rh_2$. The cells were incubated at 37° C. and aliquots withdrawn over a 24-hour period for analysis of metallopeptide concentration. Concentration of metallopeptide is plotted in FIG. 2. Peptide concentration initially dropped because of non-specific adhesion. After the initial drop, little decomposition was observed over the full 24 hours of the experiment. HPLC and ESI-MS analysis of the 24-hour aliquot confirmed the presence of the starting dirhodium complex.

Figure 1:
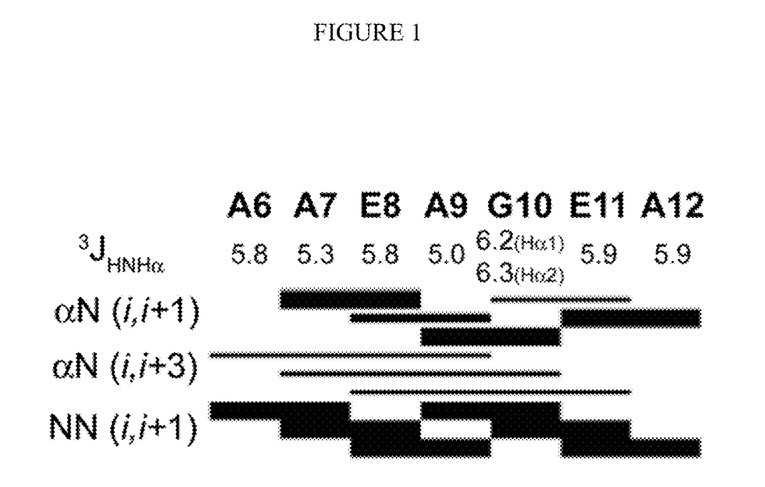
FIG. 1. $^3J_{HN-HA}$ coupling constants and nuclear Overhauser effect (NOE) connectivity for the metal-binding region of the EE3G-Rh$_2$(OAc)$_2$ complex. The NOE intensity is represented by line thickness.
Figure 2:
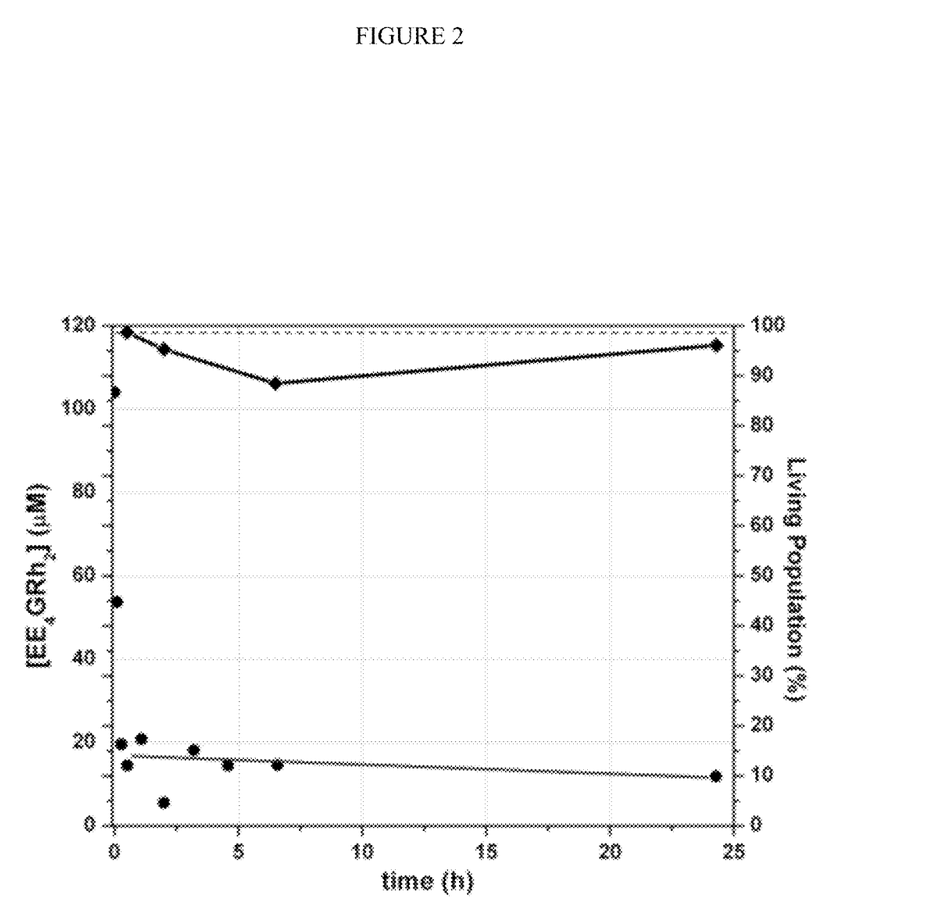
FIG. 2. Biocompatibility analysis of cis-EE4G-Rh$_2$(OAc)$_2$ (100 mM) incubated with HEK-293 cells. EE4G-Rh$_2$ stability time course and cell viability of control (dashed line) and metallopeptide-treated (solid line) cells.

Cell viability and population size assays were made over a 24-hour period using a hemocytometer and tryptan blue stain (FIG. 2). The metallopeptide-treated cells reproduced over the first 2 hours and the number of dead cells minimally increased. After 6 hours, cell population remained at 220K with a small increase in dead cells (12%). Over the remaining time, treated cells recovered to levels comparable to the control despite the metallopeptide (about 10 mM) in the media. Cell viability data were further confirmed by brightfield and fluorescence microscopies (not shown), confirming that dirhodium metallopeptides are stable in a cellular environment and are tolerated by living cells.

EXAMPLE 3

Metallopeptide Catalytic Activity

Figure 3:
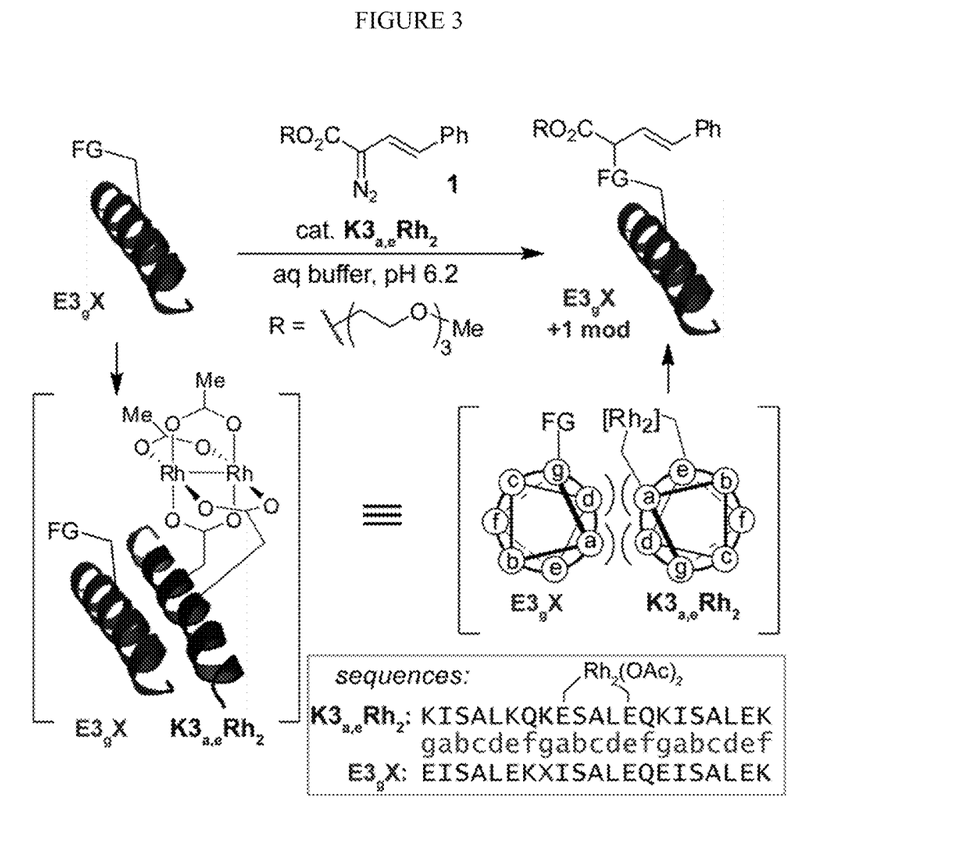
FIG. 3. (SEQ ID NOS: 1 and 2) Catalytic covalent modification of amino acid side chains can be achieved using coiled-coil assembly to localize a dirhodium metallopeptide to a specific side chain of a substrate peptide. FG refers to a amino acid side chain, 1 is the 2-styryl-2-diazoacetate ester.

Model peptides were tested against an exemplary diazo compound (2-styryl-2-diazoacetate esters) shown as reagent 1 in FIG. 3.

Dirhodium tetracarboxylates are an attractive choice for examining peptide-induced selectivity in organometallic catalysis because the dirhodium center is known to catalyze X—H and C—H insertions in water, including those of the indole side chains of tryptophan residues. In addition, dirhodium metallopeptides bound to side-chain carboxylates are stable with respect to ligand exchange in water at pH≦7.6.

We turned to the coiled coil, a simple and robust peptide assembly, to provide molecular recognition. Coiled-coils mediate essential protein-protein interactions, and peptides that interact with natural coil domains, inhibiting protein-protein interactions, have been described. Coiled-coil sequences feature a heptad repeat (labeled abcdefg) with hydrophobic residues in positions a and d to create a hydrophobic interface along one side of an α-helix, facilitating assembly into dimeric or higher-order structures. The design principles for heterodimeric pairs are well established, such as the E3/K3 pair, in which complementary charges in the positions that flank the interface, e and g, select for heterodimerization of the lysine-rich K3 and glutamate-rich E3 peptides.

As shown in FIG. 3, we envisioned that a metallopeptide $K3_{a,e}Rh_2$, in which the peptide is bound to a dirhodium center through two glutamate side chains, might deliver the dirhodium catalyst to the site of a reactive side chain, facilitating covalent modification of the target peptide. Binding the dirhodium center at positions a and e ensures that the metal will be held proximal to the coil-coil interface, and the a, e spacing serves to stabilize the necessary helical structure. The E3/K3 parent for the sequences used here form simple dimers with Kd of about 9 μM. The presence of a bridging dirhodium center in $K3_{a,e}Rh_2$ does not significantly alter these properties, as judged by circular dichroism, Job plot analysis, and thermal denaturation experiments (not shown).

Peptide substrates designed to interact with a metallopeptide catalyst through coiled-coil assembly were prepared based on a lysine rich coiled-coil assembly K3, which positions a dirhodium center on metallopeptide $K3_{a,e}Rh_2$ near position g of the complementary peptide $E3_gX$ (FIG. 3). $K3_{a,e}Rh_2$ is KISALKQKESALEQKISALEK(SEQ ID No: 1)-(Rh$_2$(OAc)$_2$) adduct, and $E3_gX$ is EISALEKXIS-ALEQEISALEK (SEQ. ID NO: 2). Covalent modification of variable residue g was then examined.

Remarkably, over half of the natural amino acids can be covalently modified with the diazo reagent 1 (see Table 2). In addition to aromatic residues (entries 1-3), cysteine, glutamine, asparagine, arginine, and glutamic acid are each modified in >65% conversion within 24 h of reaction with metallopeptide catalyst $K3_{a,e}Rh_2$ and diazo reagent 1 (entries 4-7, 9). Several other residues—aspartic acid, serine, histidine, and lysine—showed modest conversion (entries 8, 10-12). Relative modification rates ($k_{rel}$) were based on conversion at 1 hour, which corrects for catalyst loading and assumes first-order catalysis. Aromatic side chains (entries 1-3, 11) span an especially large range of reactivity. Modification was not observed for threonine, methionine, or any hydrocarbon side chain (entries 13-16).

MS/MS fragmentation analysis verified the site of covalent modification. In most cases, the product mass indicated a simple adduct of the starting material and the carbene derived from diazo 1. With arginine, the modified product had a mass consistent with loss of the polyethylene glycol alcohol, likely forming an imidazolone.

TABLE 2

Covalent modification of E3gX peptidesa

| entry | E3gX X = | mol % $K3_{a,e}Rh_2$ | product[b] | % conv. at 24 h[c] | $k_{rel}$[d] |
|---|---|---|---|---|---|
| 1 | Trp | 1 |  | >95 (10:13)[e,f] | 3000 |
| 2 | Tyr | 10 |  | >95 (7:1)[g] | 100 |
| 3 | Phe | 10 |  | >95 (8:1)[g] | 87 |

TABLE 2-continued

Covalent modification of E3gX peptides[a]

| entry | E3gX X = | mol % K3$_{a,e}$Rh$_2$ | product[b] | % conv. at 24 h[c] | k$_{rel}$[d] |
|---|---|---|---|---|---|
| 4 | Cys | 10 | (structure: S-CH(CO$_2$R)-CH=CH-Ph) | 78 (5:1) | 560 |
| 5 | Gln | 10 | (structure: (CH$_2$)$_{1,2}$-C(=O)-NH-CH(CO$_2$R)-CH=CH-Ph) | >95[f] | 260 |
| 6 | Asn | 10 | | 70 | 110 |
| 7 | Glu | 20 | (structure: (CH$_2$)$_{1,2}$-C(=O)-O-CH(CO$_2$R)-CH=CH-Ph) | 76 (9:1)[g] | 130 |
| 8 | Asp | 20 | | 53 (5:1)[g] | 100 |
| 9 | Arg | 50 | (structure: (CH$_2$)$_3$-NH-C(=N)-NH-C(=O)-CH-CH=CH-Ph, imidazolinone) | 73 (6:2)[e,g] | 100 |
| 10 | Ser | 50 | (structure: CH$_2$-O-CH(CO$_2$R)-CH=CH-Ph) | 28[g] | 40 |
| 11 | His | 50 | (structure: imidazole-N-CH(CO$_2$R)-CH=CH-Ph) | 17[g] | 20 |
| 12 | Lys | 50 | (structure: (CH$_2$)$_3$-NH-CH(CO$_2$R)-CH=CH-Ph) | 8[g] | 20 |
| 13 | Thr | 50 | — | NR | — |
| 14 | Val | 50 | — | NR | — |
| 15 | Ala | 50 | — | NR | — |
| 16 | Met | 50 | — | NR | — |

[a]Reacted 50 μM substrate and 2.5 mM diazo 1 in aqueous buffer (pH 6.2) at room temperature, unless otherwise noted.
[b]Proposed structures are based on small-molecule precedent.
[c]Conversion based on MALDI-TOF MS analysis of the reaction mixture. Numbers in parenthesis indicate ratio of singly modified to doubly modified peptide, if doubly modified species were observed.
[d]Based on initial rate measurements of product formation at 1 hour and corrected for catalyst concentration.
[e]Less than 10% of triply modified peptide was observed.
[f]Reaction time was 6 hours.
[g]10 mM diazo 1 added in two portions.

EXAMPLE 4

Catalysis with Natural Proteins

The prior example demonstrated that model peptides could be successfully modified with the diazo reagent 1 using the metallopeptide catalyst. This example applies that reaction chemistry to natural proteins, both as the target and as the catalytic peptide.

Metallopeptide Jun(Rh$_2$) was prepared based on an affinity-optimized c-Jun variant with glutamate residues in g and d positions. The target was the bZip domain of c-Fos, an oncogene product that regulates transcription by forming a heterodimeric coiled coil with c-Jun.

Purified Jun variant was metalated with Rh$_2$(OAc)$_2$(tfa)$_2$ in aqueous buffer. Isolation of the Jun(Rh$_2$) metallopeptide was challenging due to its poor solubility. In initial studies at 4° C., crude Jun(Rh$_2$) directly from the metalation process could be used in modification reactions with activity identical to that of purified material, thus avoiding time-consuming and unnecessary material loss that accompanied isolation.

Figure 4:
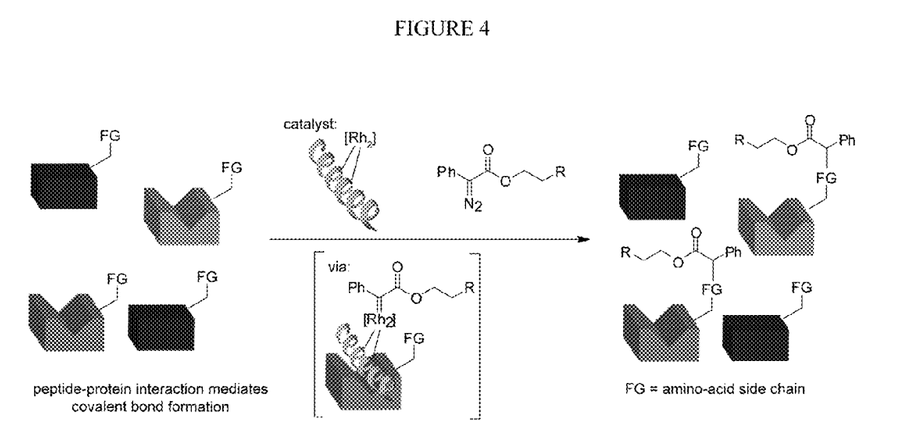
FIG. 4. General schematic showing RH$_2$ metallopeptide catalysis.

Covalent modification of c-Fos (100 μM) with 1 equivalent of Jun(Rh$_2$) at room temperature resulted in 17% conversion after 24 hours with the diazo reagent 1. But, because these coiled coils are more stable at lower temperatures, as evidenced by CD spectral data, decreasing the temperature and adding Jun(Rh$_2$) and diazo 1 in small portions afforded 32% conversion in 45 h at 4° C. and 88% conversion over the same time period at −15° C. (FIG. 4A).

Figure 5:
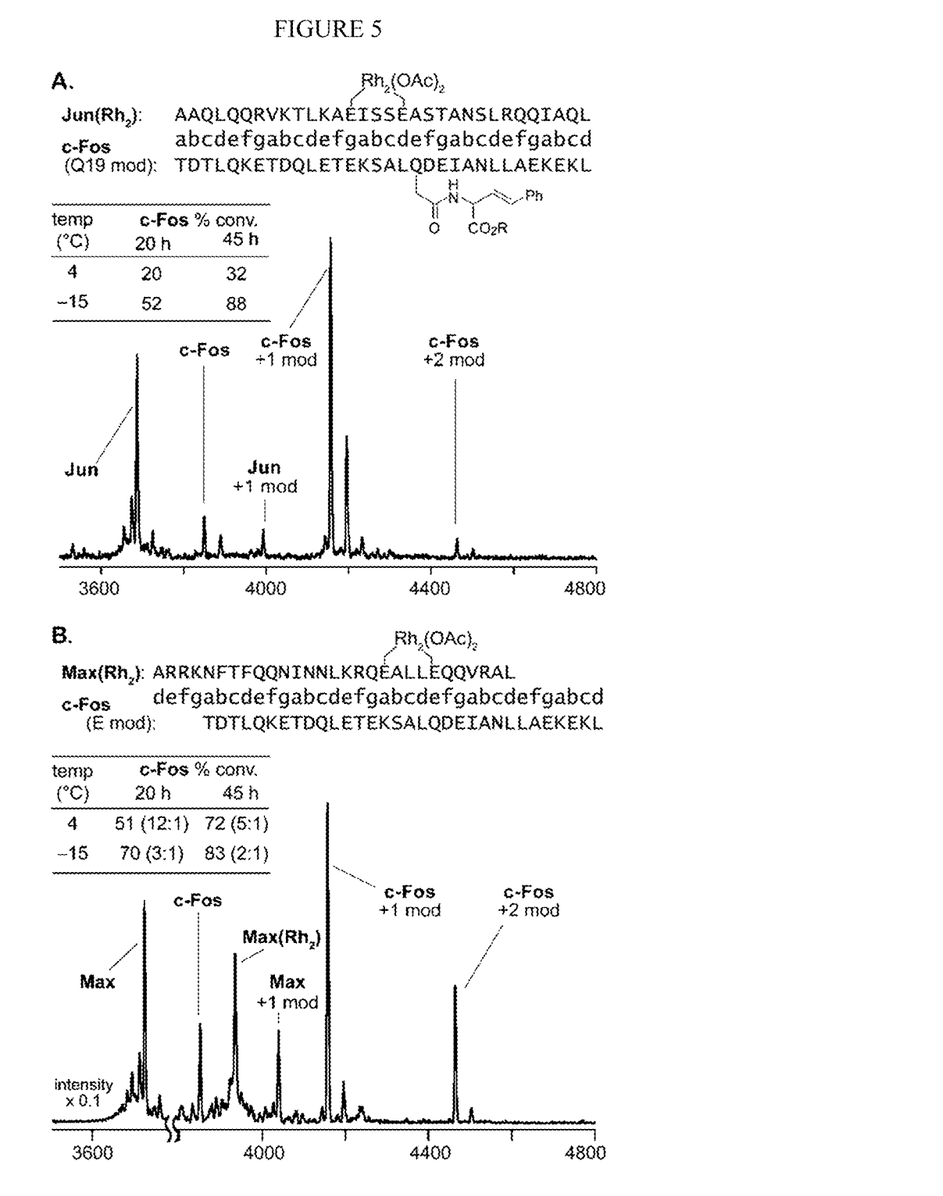
FIG. 5. MALDI-TOF MS spectra of c-Fos (SEQ ID NO: 15) modification catalyzed by Jun(Rh2) (A) (SEQ ID NO: 14) and Max(Rh2) (B)(SEQ ID NO: 16). Reactions were 100 μM in substrate at pH 6.5. Metallopeptide and diazo 1 were added portion-wise to final concentrations of 200 μM and 5 mM, respectively. Sequences illustrate the expected alignment of the coiled coils and the site of modification (B) In the inset table, the ratio in parentheses indicates the ratio of singly to doubly modified product.

Catalytic activity was also investigated for a second metallopeptide based on the leucine-zipper Max. Although Max is not reported to be a ligand for c-Fos, the corresponding metallopeptide Max(Rh$_2$) surprisingly exhibited catalytic activity comparable to Jun(Rh$_2$), affording 72% and 83% conversion of c-Fos after 45 h at 4° C. and −15° C., respectively (FIG. 5B).

MS/MS fragmentation analysis indicated that Jun(Rh$_2$) and Max(Rh$_2$) modified different c-Fos residues. For Jun (Rh$_2$), MALDI-TOF MS/MS analysis established that Gln19 (position e) was modified. An LC-MS study further indicated two singly modified c-Fos species, which MS/MS and MS$^3$ analysis demonstrated had identical fragmentation spectra for the two species, suggesting that the product comprises two diastereomers of a single Gln19 species. In the case of Max (Rh$_2$), the dominant fragmentation pathway was cleavage of the modifying group. MALDI-TOF and LC-MS indicated that at least of the two appropriately positioned glutamate residues was modified (see FIG. 5B). Unlike Jun(Rh$_2$), Max (Rh$_2$) doubly modified c-Fos in significant quantities, suggesting that both Glu14 and Glu21 were modified.

Amazingly, site-specific reactivity can be templated on molecular recognition in interactions with such low affinities that they are uncharacterizable by available methods. Because metallopeptide Jun(Rh$_2$) has ≧100 µM affinity for Fos, reactions at 10 µM successful even though the desired Fos-Jun(Rh$_2$) dimer is not the major species. Fos-Max(Rh$_2$) reactions are comparable, displaying temperature-dependent folding behavior consistent with weak interactions (T$_M$=20° C.) that would be necessary for molecular-recognition-based modification.

EXAMPLE 5

Single COOH Metallopeptide

Figure 6:
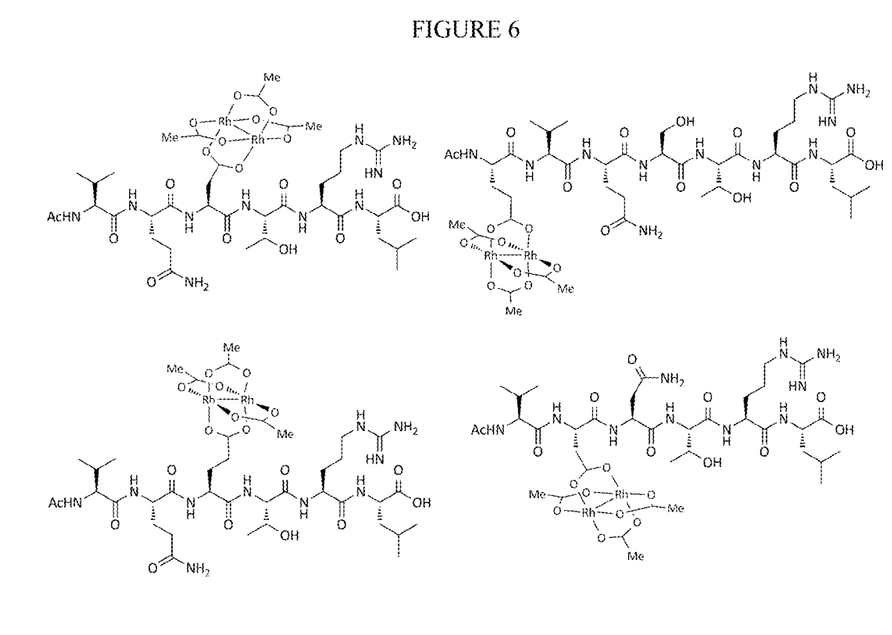
FIG. 6. Monoadduct metallopeptide catalysts, where the transition-metal complex is attached to the peptide via a single carboxylate.

The above examples employed dirhodium adducts where the rhodium was bound with two COOH residues in the protein scaffold. However, we have also performed successful catalysis where the rhodium was only held at a single COOH and the remaining position was held by an acetate (see FIG. 6). Although the data is not shown, these experiments indicate that this type of metallopeptide is also functional.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The following publications are included by reference in their entirety: U.S. Pat. No. 5,200,504.

Ramya Sambasivan and Zachary T Ball, Metallopeptides for asymmetric dirhodium catalysis, J Am Chem Soc 132: 9289 (2010).

Brian V Popp and Zachary T Ball, Structure-selective modification of aromatic side chains with dirhodium metallopeptide catalysts, J Am Chem Soc 132:6660 (2010).

Alexander N Zaykov, Brian V Popp and Zachary T Ball, Helix Induction by Dirhodium: Access to Biocompatible Metallopeptides with Defined Secondary Structure, Chem Eur J: (2010).

Alexander N Zaykov, Kevin R Mackenzie and Zachary T Ball, Controlling Peptide Structure with Coordination Chemistry: Robust and Reversible Peptide-Dirhodium Ligation, Chem Eur J 15:8961 (2009).

Scott R. Gilbertson, et al., Versatile Building Block for the Synthesis of Phosphine-Containing Peptides: The Sulfide of Diphenylphosphinoserine, J. Am. Chem. Soc. 1994, 116, 4481-4482.

Scott R. Gilbertson, et al., Structure of Phosphorus-Containing Peptide Ligands. X-ray and NMR Structural Study of Free Ligand and Rhodium Complex, J. Org. Chem. 1997, 62, 5557-5566.

Scott R. Gilbertson, et al., Synthesis of Phosphine—Rhodium Complexes Attached to a Standard Peptide Synthesis Resin, Organometallics 1996, 15, 4678-4680.

Katherine J. Franz, et al., Lanthanide-Binding Tags as Versatile Protein Coexpression Probes, ChemBio Chem 2003, 4, 265-271.

Joel T. Welch, et al., Lanthanide-binding helix-turn-helix peptides: Solution structure of a designed metallonuclease, PNAS, Apr. 1, 2003, Vol. 100, No. 7 3725-3730.

What is claimed is:

1. A catalyst comprising a transition-metal complex attached to a scaffold, werein said scaffold is a peptide, protein or peptidomimetic, wherein the transition-metal complex has Formula I, (Formula I)

wherein each X is independently O,
each R is independently alkyl,
M is Rh,
$X^1$ is a residue in said scaffold having a carboxylic acid side chain,
$X^2$ is a hydrogen, or a residue in said scaffold having a carboxylic acid side chain,
wherein said catalyst has catalytic activity in an aqueous environment, and wherein said scaffold delivers the catalyst to a target binding partner on the basis of molecular recognition of the target binding partner by the scaffold, and the catalyst induces a chemical modification of the target binding partner, said chemical modification chosen fron the group consisting of esterification, C—H activation, and cross coupling reactions.

2. The catalyst of claim 1, wherein the transition-metal complex is a dirhodium complex that catalyzes C—C or C-FG bond formation to covalently attach a reagent to said target binding partner, wherein the target binding partner is a peptide or protein and FG is an amino acid side chain in said target binding partner that has an atom capable of forming a covalent bond.

3. The catalyst of claim 2, wherein the transition-metal complex is a dirhodium complex that catalyzes C—C or C-FG bond formation to covalently attach a reagent to an amino acid chain of said target binding partner, wherein selectively amomg side chain of said target binding partner is achieved through localization of the transition-metal complex is said scaffold.

4. The catalyst of claim 1, wherein the transition-metal complex is a dirhodium complex covalently bound though equatorial carboxylate binding of one or two carboxylates in said scaffold.

5. The catalyst of claim 1, wherein said scaffold comprises only natural amino acids.

6. The catalyst of claim 1, wherein said target is a protein, peptide, or peptidomimetic.

7. A metallopeptide catalyst comprising a compound having Formula II, (Formula II)

each R is independently alkyl,
$X^1$ is a residue in a peptide scaffold having a carboxylic acid side chain; and
$X^2$ is a hydrogen or short chain alkyl, or a residue in said scaffold having a carboxylic acid side chain; and
wherein said metallopeptide catalyst modifies a target recognized by said scaffold by catalyzing reactions that chemically modify an amino acid side chain, said modification chosen from the group consisting of esterification, C—H activation and cross coupling reactions.

8. A method for modifying a target, comprising;
a. providing a catalyst comprising a compound having Formula I and attached to a scaffold, wherein the scaffold is a peptide, protein or peptidomimetic, (Formula I)

wherein each X is independently O;
each R is independently alkyl;
M is Rh;
$X^1$ is a residue in a scaffold having a carboxylic acid side chain; and
$X^2$ is a hydrogen, or a second residue in said scaffold having a carboxylic acid side chain; and
b. reacting a target with a reagent in the presence of said catalyst, wherein said scaffold recognizes and binds to said target, for a time sufficient to allow said catalyst to catalyze C—C or C-FG bond formation to covaltely attach the reagent to said target, wherein FG is an amino acid side chain in said targer that has an atom capable of forming a covalent bond.

9. A method for modifying a target, comprising;
a. providing a catalyst comprising a compound having Formula I and attached to a scaffold, wherein the scaffold is a peptide, protein of peptidomimetic, (Formula I)

wherein each X is independently O;
each R is independently alkyl;
M is Rh;
$X^1$ is a residue in a scaffold having a carboxylic acid side chain; and
$X^2$ is a hydrogen, or a second residue in said scaffold having a carboxylic acid side chain; and
b. reacting a target with a reagent in the presence of said catalyst, wherein said scaffold recognizes and binds to said target, to allow said catalyst to catalyze C—C or C-FG bond formation to covaltely attach the reagent to said target, wherein FG is an amino acid side chain in said targer that has an atom capable of forming a covalent bond.

* * * * *